(12) United States Patent
Hasegawa et al.

(10) Patent No.: US 6,361,491 B1
(45) Date of Patent: Mar. 26, 2002

(54) OPTICAL ADAPTOR FOR HIGHY PRECISION ENDOSCOPE

(75) Inventors: Hiroshi Hasegawa, Oume; Hirofumi Miyanaga; Masahiro Chiba, both of Hachioji, all of (JP)

(73) Assignee: Olympus Optical Co., Ltd. (JP)

( * ) Notice: Subject to any disclaimer, the term of this patent is extended or adjusted under 35 U.S.C. 154(b) by 0 days.

(21) Appl. No.: 09/459,664

(22) Filed: Dec. 13, 1999

(30) Foreign Application Priority Data

Dec. 15, 1998 (JP) ............................................. 10-356381
Nov. 9, 1999 (JP) ............................................. 11-318435

(51) Int. Cl.[7] ................................................. A61B 1/00
(52) U.S. Cl. ....................... 600/175; 600/111; 600/166; 600/170; 600/172; 348/45; 356/241.5
(58) Field of Search ................................. 600/111, 116, 600/172, 173, 175, 170; 348/45; 356/241.5

(56) References Cited

U.S. PATENT DOCUMENTS 5,989,185 A * 11/1999 Miyazaki ..................... 600/175

FOREIGN PATENT DOCUMENTS

JP 9-101465 4/1997
JP 11-109257 4/1999

* cited by examiner

*Primary Examiner*—John Mulcahy
(74) *Attorney, Agent, or Firm*—Ostrolenk, Faber, Gerb & Soffen, LLP

(57) ABSTRACT

An optical adaptor for an endoscope enabling an optically highly precise arrangement consists of a first frame member, a second frame member, and a distance restriction member. The first frame member is located at the distal part of the optical adaptor. A plurality of objective optical systems is stowed and held in the first frame member. The second frame member is located behind the plurality of objective optical systems. A relay optical system that transmits optical images formed by the objective optical systems and teams with an imaging optical system located in front of an imaging device in an endoscope to form an image transmission optical system is stowed and held in the second frame member. The distance restriction member is interposed between the first frame member and second frame member and thus sets the distance between the members to a predetermined value.

16 Claims, 12 Drawing Sheets

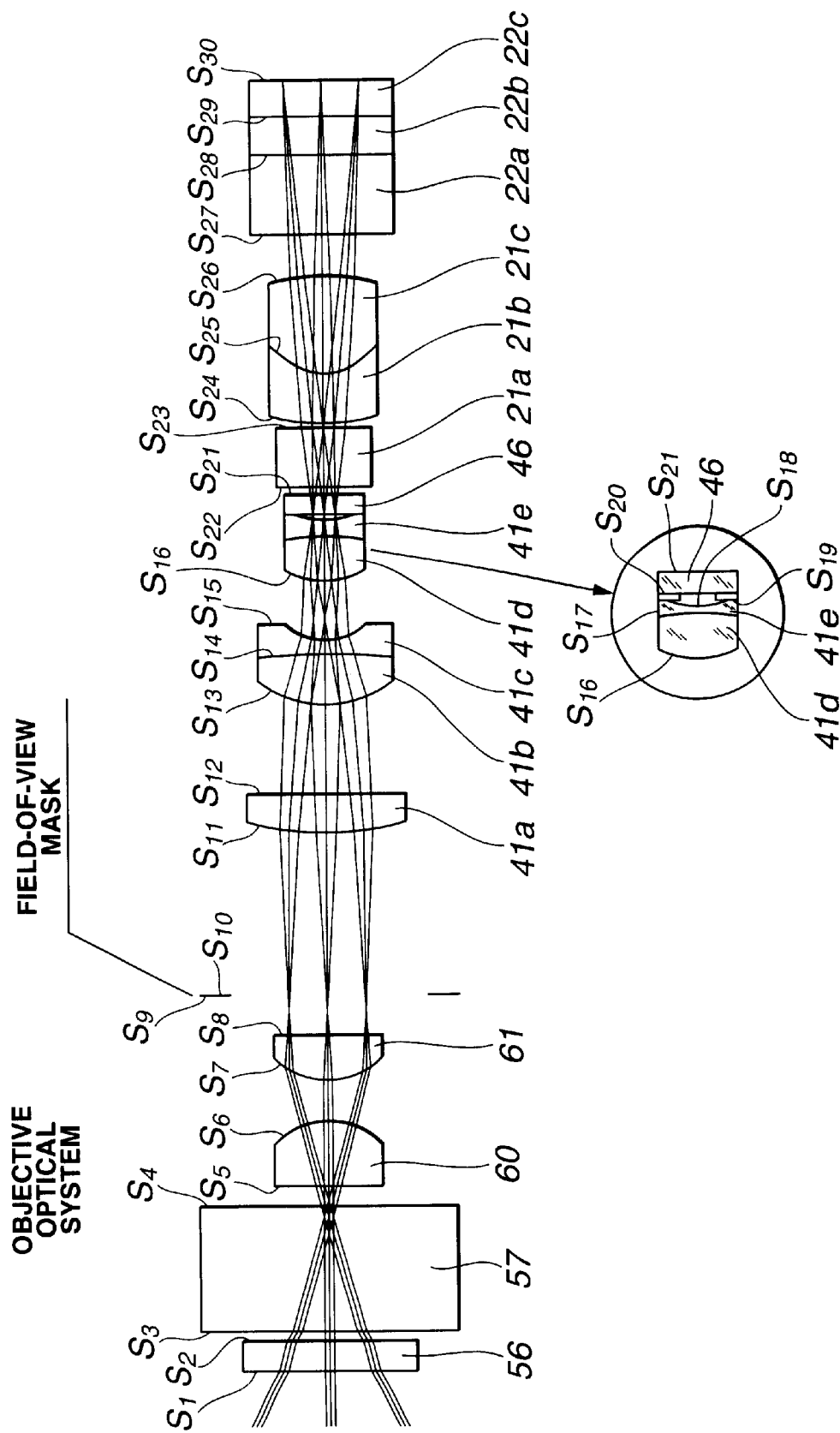

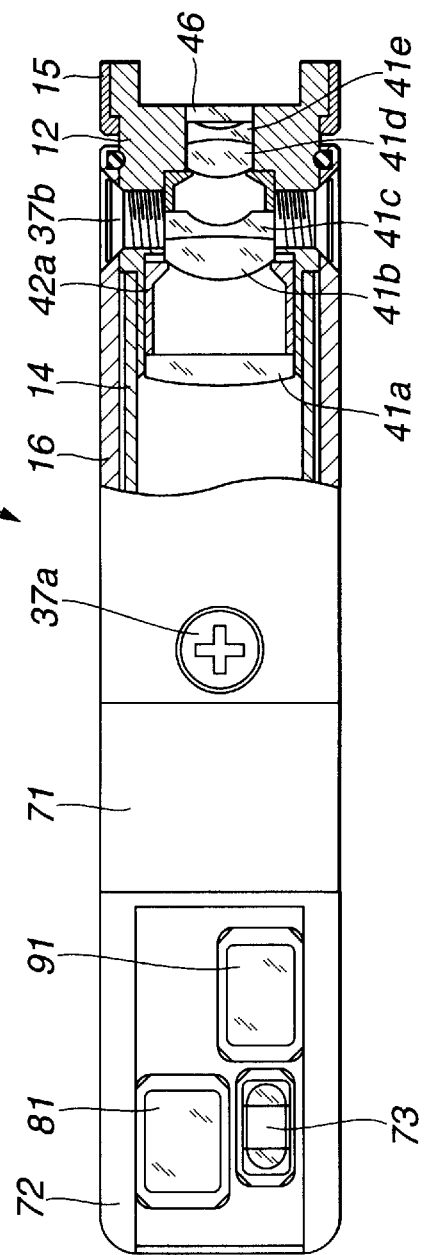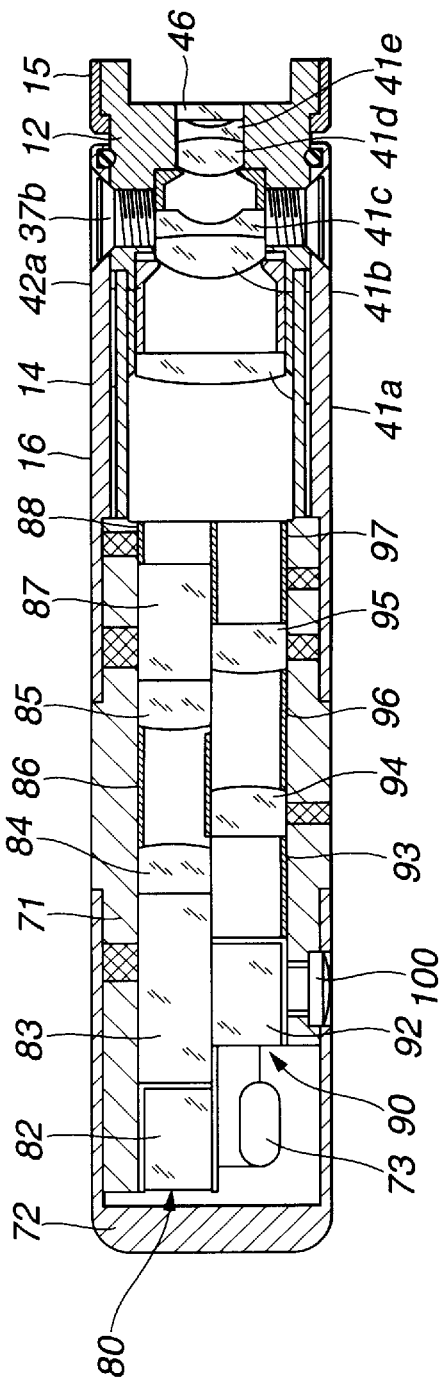

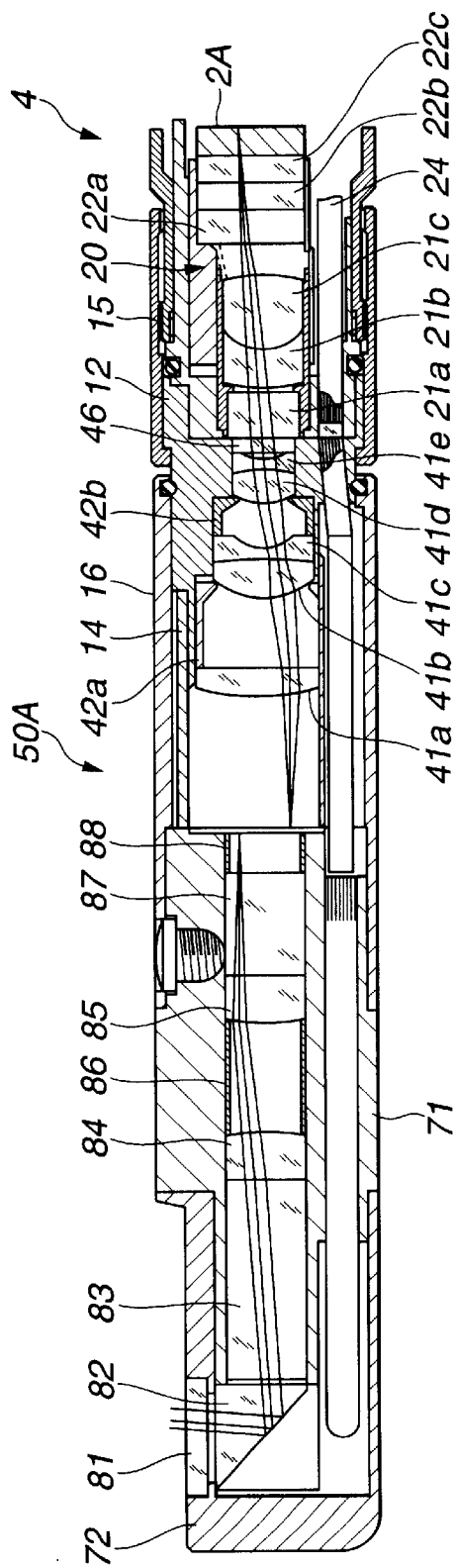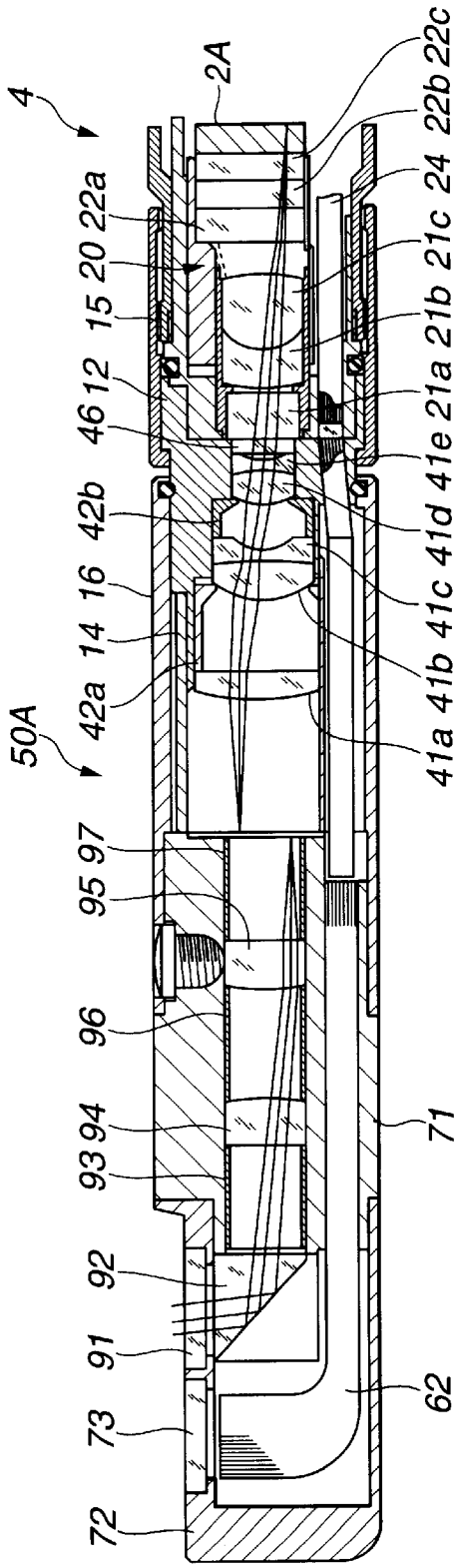

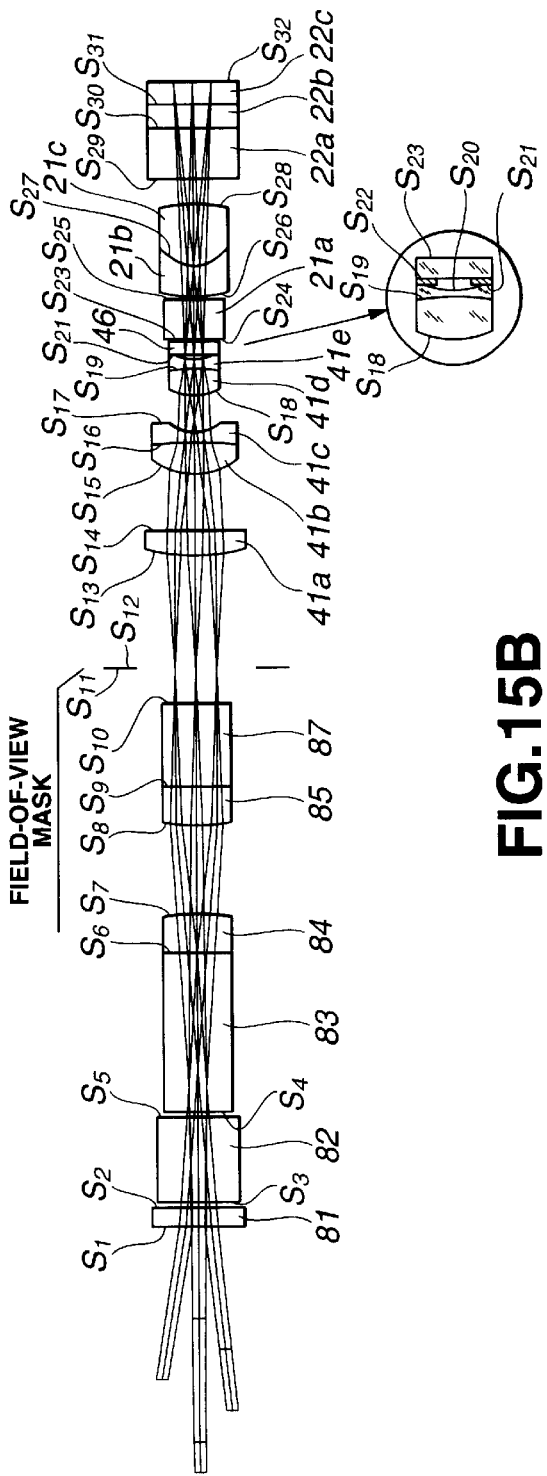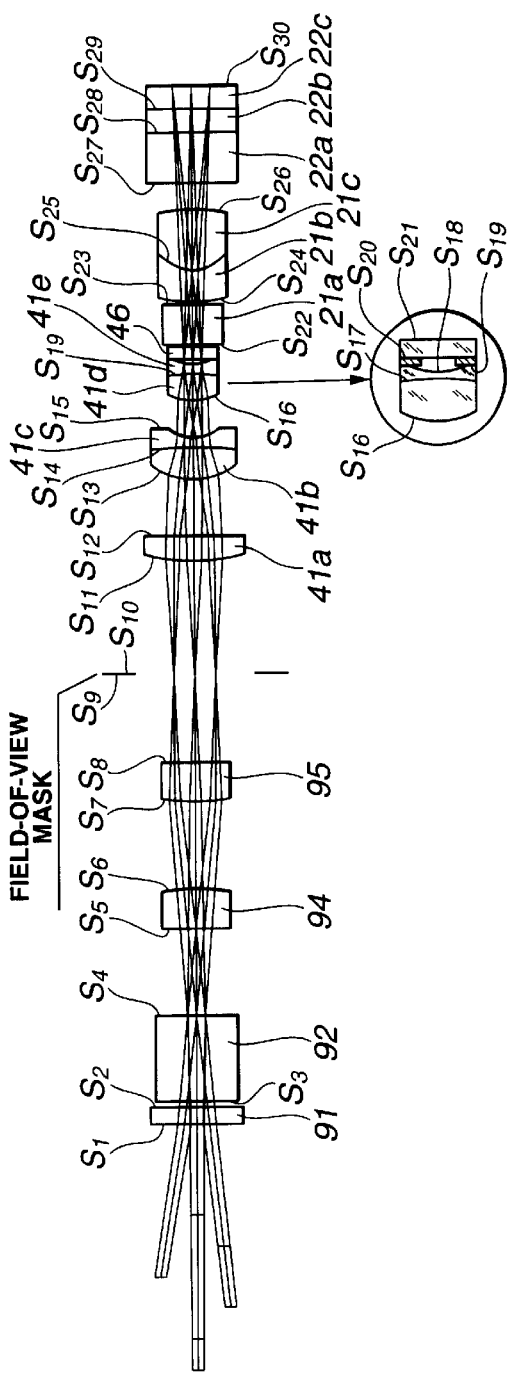

OPTICAL ADAPTOR FOR HIGHY PRECISION ENDOSCOPE

BACKGROUND OF THE INVENTION

1. Field of the Invention

The present invention relates to a high-precision optical adaptor for an endoscope that is freely detachably attached to the distal part of an endoscope.

2. Description of the Related Art

In recent years, endoscopes having elongated insertion units inserted into a body cavity for observing or treating an intracavitary organ using, if necessary, a treatment appliance passed through a treatment appliance channel therein, have been widely employed. Endoscopes for industrial use have been widely used to observe or inspect the interior of a boiler, a turbine, an engine, a chemical plant, or the like for flaws, corrosion, or the like.

The endoscopes include an electronic endoscope, having an imaging device, such as a CCD in the distal part of an insertion unit thereof. The electronic endoscope uses a display means, such as a monitor, to display an optical image of a region examined, which is projected on the imaging device, and thus enables observation of the region.

A proposed type of electronic endoscope is such that an optical adaptor having a plurality of identical or different objective optical systems is freely detachably attached to the distal part of an endoscope. A plurality of optical images of a region to be examined are concurrently projected on an imaging device incorporated in an insertion unit via the optical adaptor.

For improving the optical characteristics of the optical adaptor, for example, Japanese Unexamined Patent Publication No. 11-109257 entitled "Imaging optical system of an endoscope" disclosed an optical adaptor. An optical adaptor is composed of a plurality of identical or different objective optical systems, and one relay optical system for transmitting a plurality of images formed by the objective optical systems.

In the imaging optical system of an endoscope, an adaptor having objective optical systems, which share the same specifications, arranged therein is attached in order, not only merely to perform an endoscopic examination, but also to measure an object according to a known trigonometric survey method. For measurement, images formed by two objective optical systems are projected onto one CCD. Measurement can be achieved highly precisely because the adaptor is designed so that the focal distance of a front group of lenses in an image transmission optical system can be varied. A large distance can therefore be preserved between objective optical systems.

By contrast, Japanese Unexamined Patent Publication No. 9-101465 disclosed the practical structure of a binocular optical adaptor as an optical adaptor for an endoscope. The binocular optical adaptor has two optical systems and transmits optical images to an imaging device, such as a CCD, located in the distal part of an insertion unit.

However, in the optical adaptor for an endoscope described in the Japanese Unexamined Patent Publication No. 9-101465, the distal part of an endoscope is located perpendicularly to an optical axis near the proximal end surface of the adaptor. The distal endoscope part has an imaging device stowage portion in which an imaging device, such as a CCD, is stowed. The imaging device requires a large stowage space compared with a system of lenses in an optical system. The outer diameter of the distal endoscope part must be large enough to preserve a space required for the imaging device stowage portion and a space required for the attaching/detaching structure of the optical adaptor. This poses a problem in that the outer diameter of the optical adaptor attachable to the distal endoscope part must be large.

Assuming that the optical adaptor disclosed in the Japanese Unexamined Patent Publication No. 11-109257 entitled "Imaging optical system of an endoscope" is adapted to an actual product, since a plurality of identical or different optical systems juxtaposed in an axial direction and one relay optical system located in tandem behind the optical systems are arranged in one adaptor, the structure of the adaptor becomes complex. Assembling therefore is difficult and introduces uncertainty. Consequently, specifications differ from product to product. When a distance between the objective optical systems and relay optical system differ from a specified distance, an observable depth is affected seriously.

Furthermore, when a side-view type adaptor is used to measure an object, images formed by two objective optical systems project at a 90° angle into the CCD using one prism. The object is then measured according to a known trigonometric survey method. For this reason, a parallax stemming from two optical axes cannot be physically increased to be equal to or larger than the diameter of the insertion unit. For highly precise measurement, the objective optical systems must be distanced well apart from each other in order to ensure a large parallax. This increases the diameter of the insertion unit.

SUMMARY OF THE INVENTION

An object of the present invention is to provide an optical adaptor for an endoscope enabling highly precise assembling despite a complex structure.

Another object of the present invention is to provide an optical adaptor for an endoscope enabling highly precise measurement of an object.

Still another object of the present invention is to provide an optical adaptor for an endoscope with a small outer diameter.

Briefly, according to the present invention, an optical adaptor for an endoscope enabling optically highly precise arrangement comprises a first frame member, a second fame member, and a distance restriction member. The first frame member is the distal part of the optical adaptor, and has a plurality of objective optical systems stowed and held therein. The second frame member is located behind the plurality of objective optical systems, and has a relay optical system stowed and held therein. The relay optical system transmits optical images formed by the objective optical systems, and cooperates with an imaging optical system of an endoscope located ahead of an imaging device to form an image transmission optical system. The distance restriction member is interposed between the first frame member and second frame member, and restricts the distance between the members to a predetermined value.

BRIEF DESCRIPTION OF THE DRAWINGS

The invention is described in detail below with reference to the following figures throughout which similar references characters denote corresponding features, consistently wherein:

FIG. 1 to FIG. 8 are views of the first embodiment of the present invention;

FIG. 1 is a perspective view of an optical adaptor for an endoscope and an endoscope;

FIG. 2A is a front elevational view of the optical adaptor for an endoscope;

FIG. 2B is a cross-sectional view of the optical adaptor for an endoscope, drawn along line 2B—2B in FIG. 2A;

FIG. 3 is a longitudinal cross-sectional view of the optical adaptor for an endoscope and the distal part of an endoscope attached thereto;

FIG. 4 is a cross-sectional view of the optical adaptor for an endoscope and the distal part of the endoscope, drawn along line 4—4 in FIG. 3;

FIG. 5 is a cross-sectional view of the optical adaptor for an endoscope and the distal part of the endoscope drawn along line 5—5 in FIG. 3;

FIG. 6A is a cross-sectional view of the optical adaptor for an endoscope and the distal part of the endoscope, drawn along line 6A—6A in FIG. 3;

FIG. 6B is a cross-sectional view of the optical adaptor for an endoscope and the distal part of the endoscope, drawn along line 6B—6B in FIG. 3;

FIG. 7 is a cross-sectional view of the optical adaptor for an endoscope and the distal part of the endoscope, drawn along line 7—7 in FIG. 3;

FIG. 8 is a schematic view of an optical path defined with the optical adaptor for an endoscope attached to the distal part of the endoscope;

FIG. 9 to FIG. 12 are views of the second embodiment of the present invention;

FIG. 9 is a longitudinal cross-sectional view of an optical adaptor, which is freely detachably attached to the distal part of an endoscope;

FIG. 10 is a longitudinal cross-sectional view of the optical adaptor for an endoscope and the distal part of the endoscope attached thereto;

FIG. 11 is a cross-sectional view of the optical adaptor for an endoscope and the distal part of the endoscope, drawn along line 11—11 in FIG. 10;

FIG. 12 is a schematic view of an optical path defined with the optical adaptor for an endoscope attached to the distal part of the endoscope;

FIG. 13A to FIG. 15 are views of the third embodiment of the present invention;

FIG. 13A and FIG. 13B are views of an optical adaptor that is freely detachably attached to the distal part of an endoscope;

FIG. 13A is a side elevational, particularly cross-sectional, view of an optical adaptor;

FIG. 13B is a cross-sectional view of the distal part of the optical adaptor shown in FIG. 13A;

FIG. 14A and FIG. 14B are longitudinal cross-sectional views of the optical adaptor and the distal part of an endoscope attached thereto;

FIG. 14A is a cross-sectional view of a first objective optical system;

FIG. 14B is a cross-sectional view of a second objective optical system;

FIG. 15A and FIG. 15B are schematic views of optical paths defined with the optical adaptor for an endoscope attached to the distal part of an endoscope;

FIG. 15A is a schematic view of an optical path defined by one objective optical system; and FIG. 15B is a schematic view of an optical path defined by another objective optical system.

DESCRIPTION OF THE PREFERRED EMBODIMENTS

Embodiments of the present invention will be described with reference to the drawings below.

Referring to FIG. 1 to FIG. 8, the first embodiment of the present invention will be described.

Figure 1:
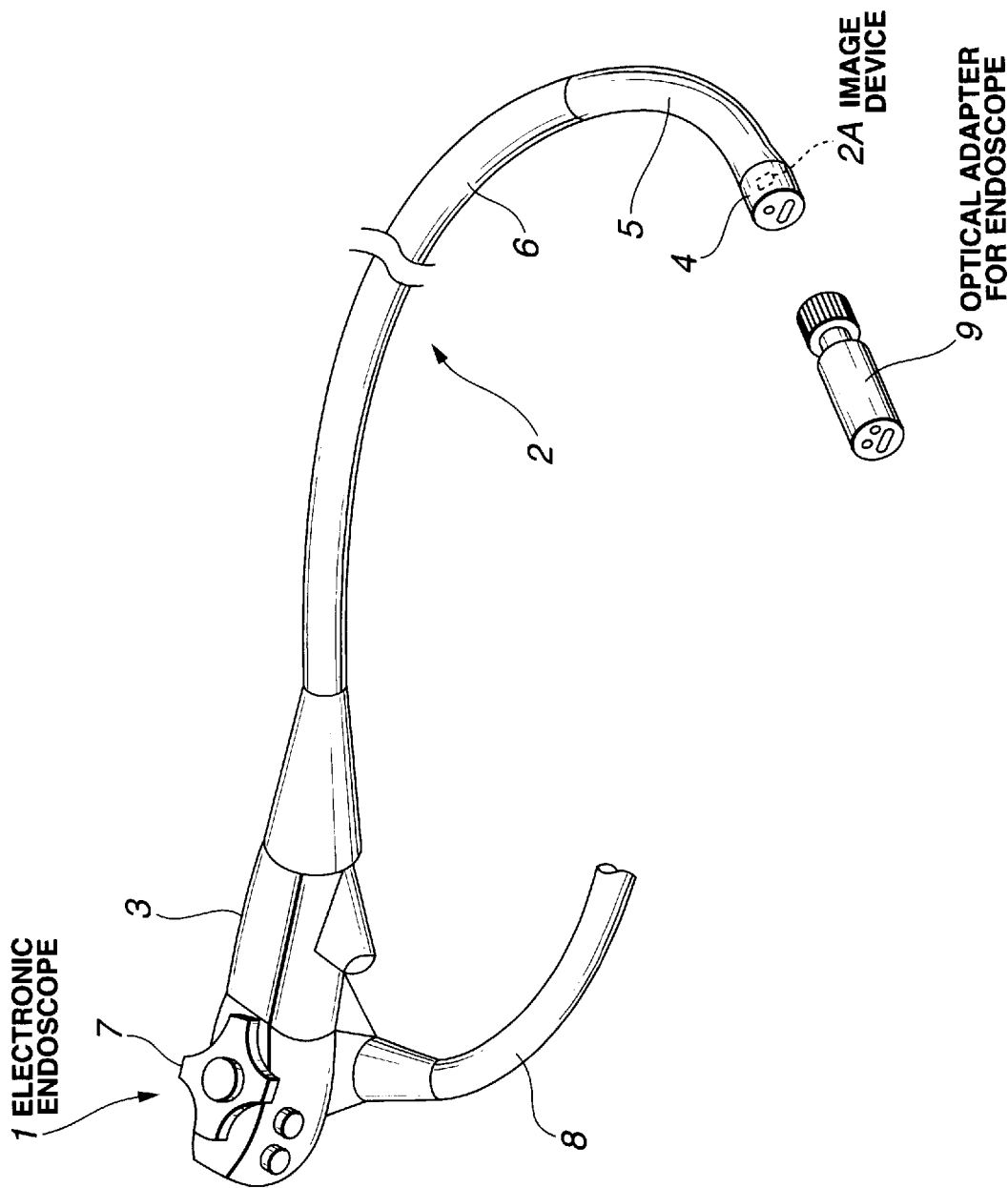

As shown in FIG. 1, an electronic endoscope (hereinafter, endoscope) 1 is designed to be coupled to a light source apparatus and a video signal processing apparatus(not shown) so that the endoscope can be uncoupled freely. An imaging device 2A, such as a CCD, is incorporated in the distal part of an elongated insertion unit 2 of the endoscope 1. An electric signal carrying an optical image of a region examined and output from the imaging device 2A is processed by the video signal processing apparatus. A resultant video signal is output to a display means, such as a monitor, whereby an endoscopic image is displayed for observation of the region.

The endoscope 1 consists mainly of an elongated insertion unit 2 having the imaging device 2A incorporated in the distal part thereof, and a hand-held operation unit 3 communicating with the proximal end of the insertion unit 2. The insertion unit 2 consists of a distal part 4, a freely bendable part 5 communicating with the distal part 4, and an elongated, flexible soft part 6 communicating with the bendable part 5. The operation unit 3 has an angling lever 7 used to angle the bendable part 5. A universal cord 8 extends from the flank of the operation unit 3. The universal cord 8 and the light source apparatus and video signal processing apparatus (not shown) are coupled to the endoscope 1 via connectors (not shown).

An optical adaptor for an endoscope (hereinafter, optical adaptor) 9 is freely detachably attached to the distal part 4 of the insertion unit 2. The optical adaptor of the present embodiment is a binocular-type optical adaptor, having two objective optical systems, which share the same specifications, arranged in the distal part thereof.

The optical adaptor 9 will be described with reference to FIG. 2A to FIG. 6.

Figures 2A, 2B:
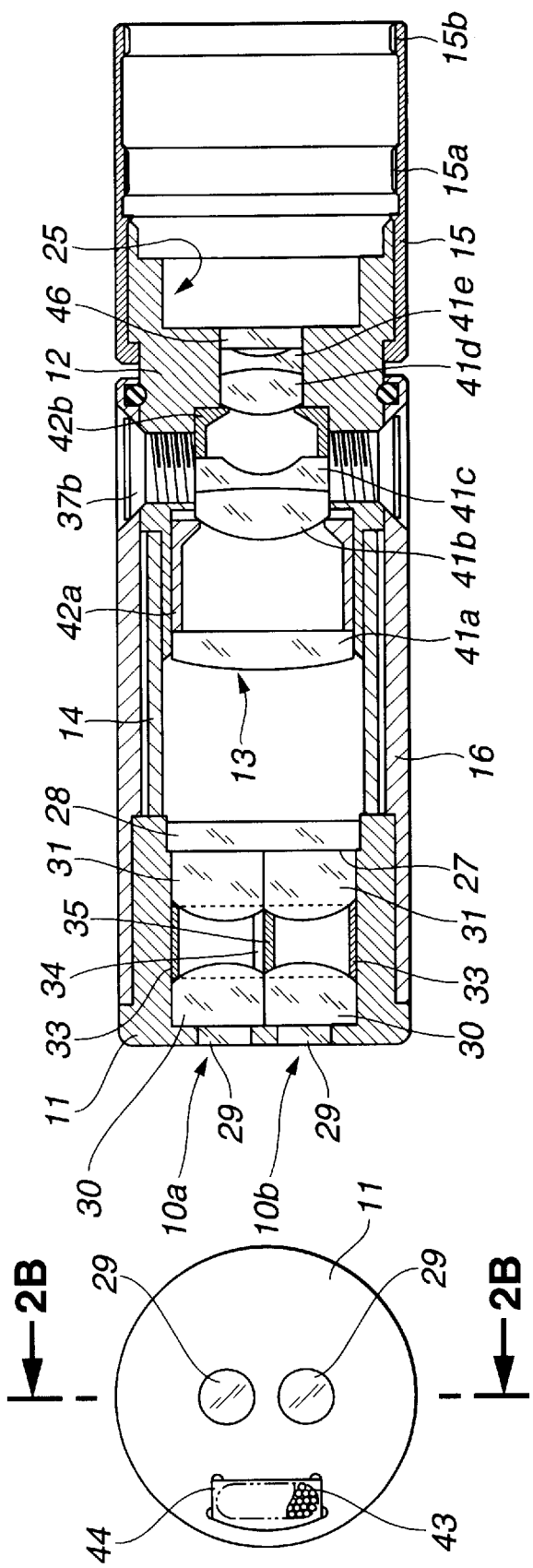
FIG. 2A and FIG. 2B are views of the optical adaptor for an endoscope.
Figure 3:
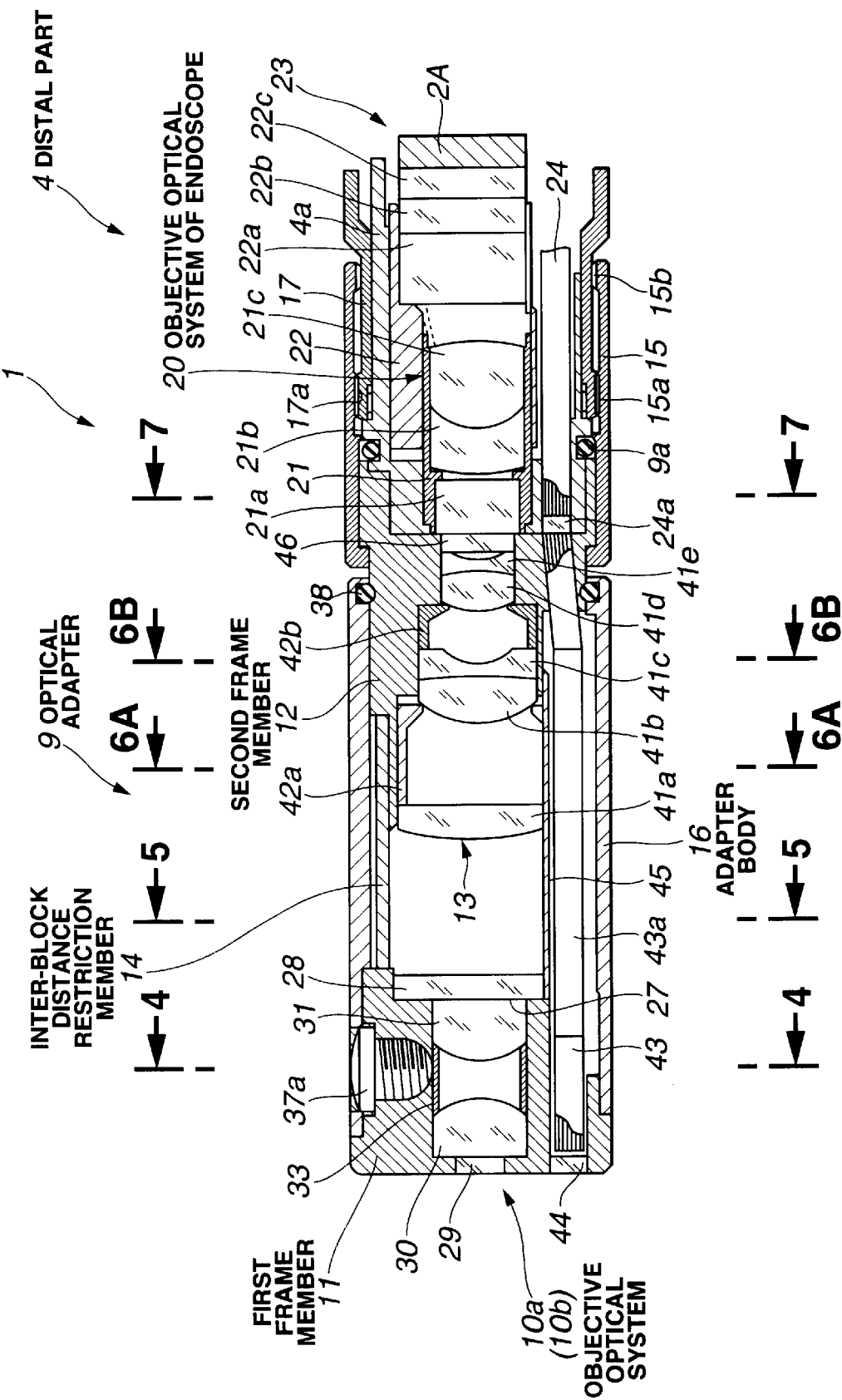

As shown in FIG. 2A, FIG. 2B, and FIG. 3, the optical adaptor 9 consists mainly of a first frame member 11, a second frame member 12, a distance restriction member 14, an adaptor attachment/detachment member 15, and an adaptor body 16. The first frame member 11 is shaped like a cylinder and serves as the distal part of the optical adaptor. The first frame member 11 has two objective optical systems 10a and 10b stowed with a predetermined distance preserved between the optical axes thereof. The second frame member 12 is shaped like a pipe and is located behind the first frame member 11 and has a relay optical system 13 stowed therein. The relay optical system 13 transmits optical images of a region to be examined, which are formed by the two objective optical systems 10a and 10b, to an imaging optical system in the endoscope 1, described later. The distance restriction member 14 sets the distance between the second frame member 12 and first frame member 11 to a predetermined value. The adaptor attachment/detachment member 15 is shaped like a pipe and acts as a coupler to freely detachably attach the optical adaptor 9 to the distal endoscope part 4. The adaptor body 16 is a pipe-shaped cover member in which the first frame member 11, second frame member 12, and distance restriction member 14 are encapsulated as a unit.

A pair of cover glasses 29 in the objective optical systems 10a and 10b is mounted on the distal surface of the first frame member 11 so that a region located in a direction of insertion can be observed. In short, the optical adaptor 9 is designed to pick up an optical image of a region to be examined that is located in a direction of direct view. An illumination cover glass 44 for emitting light is located on the left-hand side of the pair of cover glasses 29 in FIG. 2A. The distal surface of an adaptor light guide fiber bundle 43, over which light is transmitted, abuts on the proximal surface of the illumination cover glass 44. The adaptor light guide fiber bundle 43 is sheathed with an armor tube 43a made of, for example, a resin.

The two objective optical systems 10a and 10b, sharing the same specifications and lying in the first frame member 11, are each composed of the two cover glasses 29, two distal plano-convex lenses 30, two rear plano-convex lenses 31, and one cover glass 28 that are arranged in that order from the distal end of the optical adaptor. The cover glasses 29 are formed with transparent planar parallel plates. The distal plano-convex lenses 30 located at the distal part of the optical system each have one end thereof formed as a convex surface and the other end thereof formed as a flat surface. The rear plano-convex lenses 31 located at the rear part of the optical system have substantially the same shape as the distal plano-convex lenses 30. The cover glass 28 is formed with a transparent planar parallel plate. Two distance rings 33 for restricting the distances between two pairs of the plano-convex lenses 30 and 31 are interposed between the distal plano-convex lenses 30 and rear plano-convex lenses 31. A mask 27 shaped like a thin plane is located at the same position as the image planes of the objective optical systems 10a and 10b at which the front surface of the cover glass 28 is located.

The cover glasses 29, distal plano-convex lenses 30, distance rings 33, rear plano-convex lenses 31, mask 27, and cover glass 28 are locked and held using an adhesive and thus prevented from moving within the first frame member 11.

Figure 4:
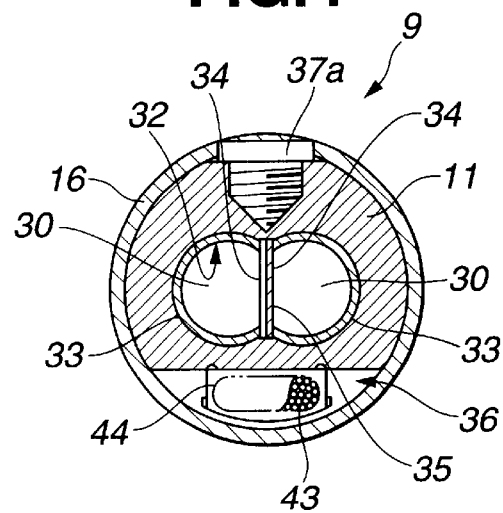

As shown in FIG. 4, the first frame member 11 has a section thereof shaped substantially like a letter D. A space portion 36 is created between the flat surface of the first frame member 11 and the inner circumference of the adaptor body 16. The guide fiber bundle 43 sheathed with the armor tube 43a is passed through the space portion 36.

The pair of distal plano-convex lenses 30 and the pair of rear plano-convex lenses 31 in the objective optical systems 10a and 10b have sections shaped substantially like the letter D. The plano-convex lenses 30 and 31 are stowed in a plano-convex lens stowage portion 32 that is a through hole shaped substantially like a numeral 8.

Specifically, the distal plano-convex lenses 30 and rear plano-convex lenses 31 are stowed in the plano-convex lens stowage portion 32 with opposed flat surfaces thereof brought into close contact. The outer circumferences of the plano-convex lenses 30 and 31 are painted in, for example, black for the purpose of intercepting light. Light interception is needed for preventing flare or the like that occurs when incident light coming from outside of a field of view or light reflected from an inner surface invades from one objective optical system into the other objective optical system.

The distance rings 33 are each formed with a pipe member having a section that is shaped substantially like a letter C. The distance rings 33 have stepped portions 34 formed on opposed open sides thereof that extend in an axial direction. A plate member 35, shaped substantially like a rectangle and having the ability to intercept light, is placed on one of the stepped portions 34, thus blocking the open sides of the distance rings that extend in the axial direction. Owing to this structure, similarly to the black paint, incident light from outside of a field of view or light reflected from an inner surface is prevented from invading from one objective optical system to the other objective optical system. A distal locking screw 37a is used to secure the first frame member 11 and adaptor body 16 as a unit.

Figure 5:
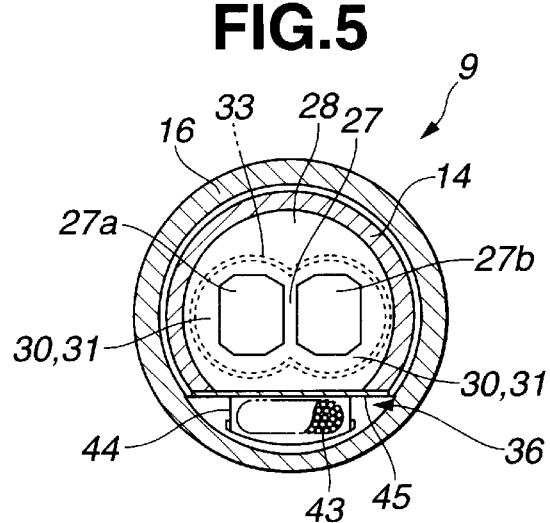

As shown in FIG. 5, the mask 27 and cover glass 28 have sections thereof shaped substantially like the letter D. The mask 27 has two octagonal openings 27a and 27b therein. Light passing through the two openings 27a and 27b clearly delineates the contours of the openings on the imaging surface of the imaging device 2A. In other words, optical images passing through the objective optical systems 10a and 10b are clearly projected on the imaging surface of the imaging device 2A. Consequently, an endoscopic image clearly expressing the contour of a peripheral region can be displayed on the screen of the monitor.

The distance restriction member 14 is formed with a pipe member having a section that is shaped substantially like the letter C. The open side of the distance restriction member 14 extending in an axial direction is blocked with a partition plate 45 shaped substantially like a rectangle and having the ability to intercept light. The distal end of the partition plate 45 abuts on the flat surface of the cover glass 28. The partition plate 45 and the inner circumference of the adaptor body 16 define the space portion 36 which receives the guide fiber bundle 43.

Figure 6A:
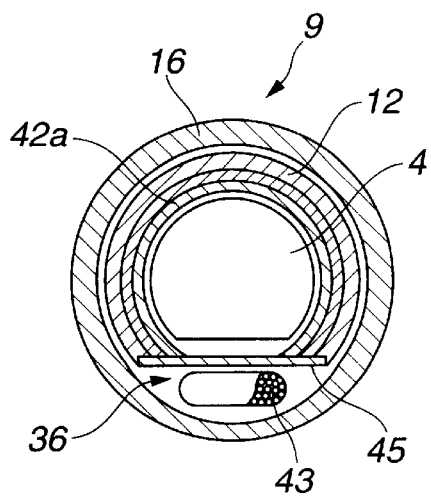
FIG. 6A and FIG. 6B are views of a second frame member and a relay optical system.
Figure 6B:
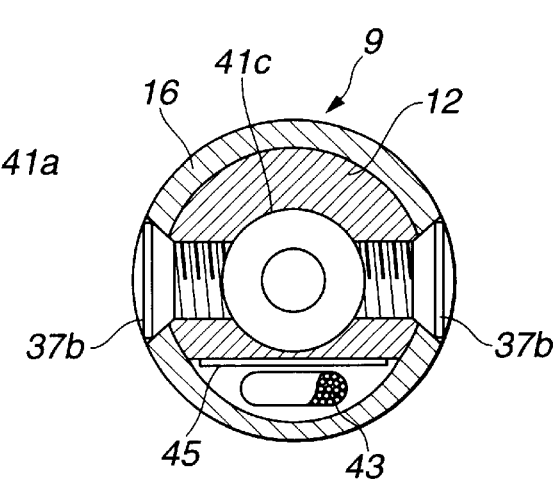

As shown in FIG. 6A and FIG. 6B, the second frame member 12 has a section shaped substantially like the letter D. The second frame member 12 has a through hole as the center portion thereof. A group of lenses forming a relay optical system is arranged in the through hole. A distal part placement hole 25, in which the distal part 4 of the endoscope 1 is placed, is defined in the proximal part of the second frame member 12. Lenses, distance rings, and other elements constituting the relay optical system 13 are arranged in the through hole.

Specifically, the relay optical system 13 is composed of, for example, a first lens 41a, a first distance ring 42a, a second lens 41b, a third lens 41c, a second distance ring 42b, a fourth lens 41d, a fifth lens 41e, and a cover glass 46 that are arranged in that order from the distal end thereof. The cover glass 46 is formed with a transparent planar parallel plate. The lenses 41a, 41b, 41c, 41d, and 41e, the distance rings 42a and 42b, and the cover glass 46 are locked and held using an adhesive and thus prevented from moving within the second frame member 12.

The section of the first lens 41a is shaped substantially like the letter D. The section of the first distance ring 42a is shaped substantially like the letter C. The partition plate 45 is placed and locked in order to block the open side of the first lens 41a, that is, the flat surface of the first lens 41a and the open side of the first distance ring 42a which extend in an axial direction.

Light causing flares may leak out from the guide fiber bundle 43 in the space portion 36 defined by the partition plate 45 and the inner circumference of the adaptor body 16. However, the foregoing structure prevents the light causing flares from falling on the cover glass 28 and the distance restriction member 14 in the first frame member 11, and the first lens 41a and the first distance ring 42a in the second frame member 12. The inclusion of the partition plate 45 also prevents invasion of dust from the space portion 36.

A proximal locking screw 37b is used to secure the second frame member 12 and adaptor body 16 as a unit. A seal member 38 in FIG. 3 is an O ring or the like for sealing the adaptor body 16 and second frame member 12 in a watertight manner.

The adaptor attachment/detachment member 15, shown in FIG. 2B, is mounted on the outer circumference of the second frame member 12 so that the adaptor attachment/detachment member 15 can rotate freely. Female threads 15a and 15b are threaded on the inner circumference of the adaptor attachment/detachment member 15. The female threads 15a and 15b are meshed with a male thread 17a, described later, threaded on the outer circumference of the distal part 4 of the insertion unit 2 of the endoscope.

The adaptor body 16 and the distance restriction member 14 having a predetermined dimension are interposed between the first frame member 11 and the second frame member 12 on which the adaptor attachment/detachment member 15 is mounted. The adaptor body 16 and the second frame member 12 are threadingly secured, that is, mechanically coupled and fixed. This results in the optical adaptor 9, which is shown in FIG. 2A and FIG. 2B, having the distance between the first frame member 11 and second frame member 12 thereof restricted to a predefined value.

Next, the structure of the distal part 4 of the endoscope 1 will be described below.

As shown in FIG. 3, an objective optical system 20 serving as an imaging optical system for projecting optical images on the imaging surface of the imaging device 2A is included in the distal part 4. The objective optical system 20 in the endoscope and the relay optical system 13 in the optical adaptor 9 constitute an image transmission optical system for projecting optical images, which pass through the objective optical systems 10a and 10b, on the imaging surface of the imaging device 2A. The distal part 4 having the objective optical system 20 incorporated therein is received in the distal part placement hole 25 of the adaptor attachment/detachment member 15.

The objective optical system 20 in the endoscope is composed of a first lens frame 21 in which, for example, a plurality of optical lenses 21a, 21b, and 21c is arranged, and a second lens frame 22 mounted on the first lens frame 21. In the second lens frame 22, for example, a plurality of transparent planar parallel plates 22a, 22b, and 22c is arranged. The lens frames 21 and 22 are fixed as a unit to a distal part body 4a using an adhesive or screws (not shown).

An imaging device stowage portion 23 in which the imaging device 2A, such as a CCD, is stowed is defined at the back end of the objective optical system 20 in the endoscope. In addition to the imaging device 2A, ICs and other electrical parts and a signal cable (not shown) are stowed in the imaging device stowage portion. The imaging device stowage portion 23 therefore requires a relatively large space.

In the present embodiment, a position at which the imaging device stowage portion 23 is defined is other than a position at which the adaptor attachment/detachment member 15 is mounted on the imaging device stowage portion 23. Thus, the outer diameter of the adaptor attachment/detachment member 15 attached to the distal part 4 does not become large.

As illustrated, the light guide fiber bundle 24 over which light supplied from the light source apparatus (not shown) is propagated passes through below the objective optical system 20 in the endoscope. The distal end of the light guide fiber bundle 24 is fixed to the proximal surface of an illumination window 24a. Therefore, when the optical adaptor 9 is not attached to the distal part 4, light propagating over the light guide fiber bundle 24 passes through the illumination window 24a and emitted toward a region to be examined.

Figure 7:
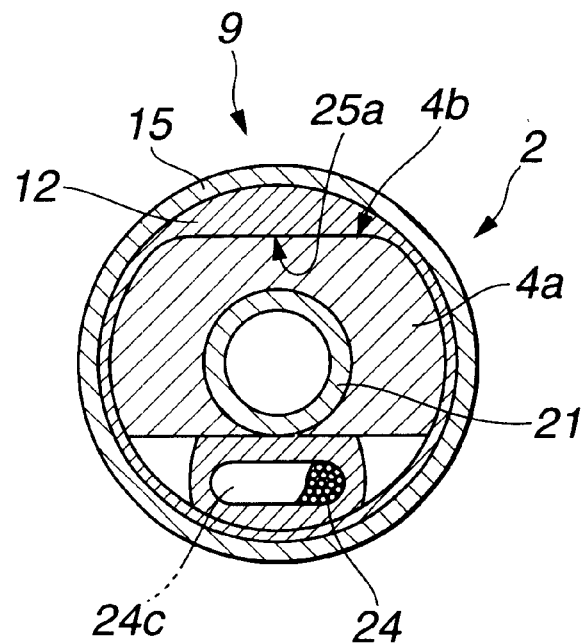
Figure 11:
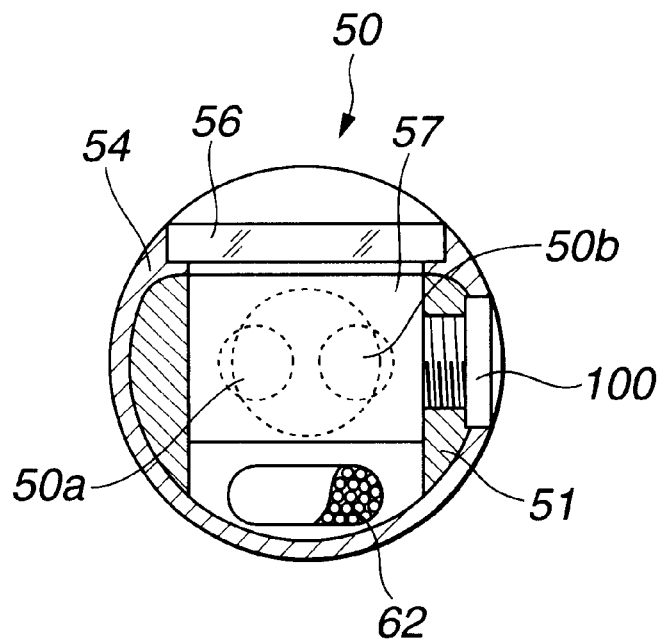

As shown in FIG. 7, when the optical adaptor 9 is attached to the distal part 4, the optical adaptor 9 and the distal part body 4a must be aligned accurately. For this purpose, the distal part placement hole 25 of the second frame member 12 in the optical adaptor 9 has a positioning surface 25a and the distal part body 4a has a flat surface 4b that meets the positioning surface 25a. When the flat surface 4b and positioning surface 25a meet, if the optical adaptor 9 is attached to the distal part 4, the optical adaptor 9 is engaged with the distal part 4 with a predetermined positional relationship established.

The female thread 16b on the inner circumference of the adaptor attachment/detachment member 15 is meshed with the male thread 17a on the outer circumference of the distal part 4 of the insertion unit 2 of the endoscope. Consequently, the optical adaptor 9 is, as shown in FIG. 3, fixed to the distal part 4. The proximal end of the adaptor light guide fiber bundle 43 is opposed to the illumination window 24a of the endoscope.

With the optical adaptor 9 attached to the distal part 4, light passing through the illumination window 24a is, as shown in FIG. 3, propagated over the adaptor light guide fiber bundle 43 in the optical adaptor 9. The light passes through the illumination cover glass 44 of the first frame member 11, toward a region to be examined.

When the optical adaptor 9 is threadingly fixed to the distal part 4 of the insertion unit 2, a seal member 9a covering the outer circumference of the distal part 4 seals the optical adaptor 9 and distal part 4 in a watertight manner. The means for coupling the optical adaptor 9 to the distal part 4 is not limited to the foregoing threading engagement. Alternatively, known bayonets may be used to freely detachably attach the optical adaptor to the distal part.

Figure 8:
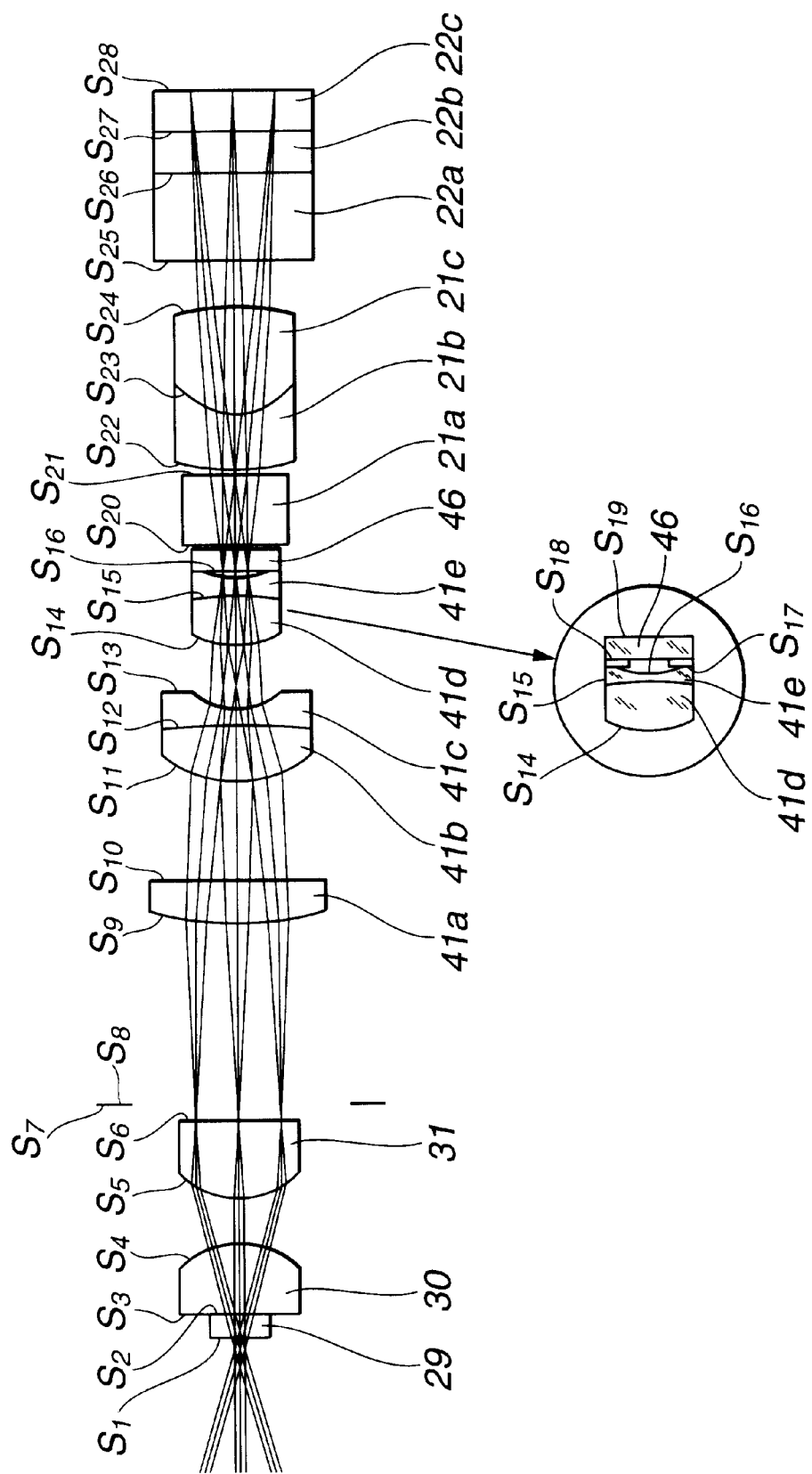

When the optical adaptor 9 is fixed to the distal part 4, as mentioned above, an optical path along which optical images acquired by the objective optical systems 10a and 10b are propagated to be projected on the~imaging device 2A is defined as shown in FIG. 8. The data of lenses will be listed below. Since the objective optical systems 10a and 10b share the same specifications, only one data set will be presented.

LENS DATA (1)
Viewing Angle (2ω) = 60°
Distance to Object = 11.7

| | | | | |
|---|---|---|---|---|
| $S_1$ | $r_1 = \infty$ | $d_1 = 0.5$ | $n_1 = 1.516$ | $v_1 = 64.15$ |
| $S_2$ | $r_2 = \infty$ | $d_2 = 0.03$ | | |
| $S_3$ | $r_3 = \infty$ | $d_3 = 1.12$ | $n_3 = 1.835$ | $v_3 = 42.72$ |
| $S_4$ | $r_4 = -2.297$ | $d_4 = 0.54$ | | |
| $S_5$ | $r_5 = 2.297$ | $d_5 = 1.12$ | $n_5 = 1.835$ | $v_5 = 42.72$ |
| $S_6$ | $r_6 = \infty$ | $d_6 = 0.74$ | | |
| $S_7$ | $r_7 = \infty$ (Field stop) | $d_7 = 0.03$ | | |
| $S_8$ | $r_8 = \infty$ | $d_8 = 3.61$ | | |
| $S_9$ | $r_9 = 7.721$ | $d_9 = 0.8$ | $n_9 = 1.883$ | $v_9 = 40.76$ |
| $S_{10}$ | $r_{10} = \infty$ | $d_{10} = 1.84$ | | |
| $S_{11}$ | $r_{11} = 2.024$ | $d_{11} = 1.03$ | $n_{11} = 1.773$ | $v_{11} = 49.60$ |
| $S_{12}$ | $r_{12} = -12.96$ | $d_{12} = 0.3$ | $n_{12} = 1.593$ | $v_{12} = 35.31$ |
| $S_{13}$ | $r_{13} = 1.009$ | $d_{13} = 1.2$ | | |
| $S_{14}$ | $r_{14} = 1.686$ | $d_{14} = 0.88$ | $n_{14} = 1.773$ | $v_{14} = 49.60$ |
| $S_{15}$ | $r_{15} = -4.362$ | $d_{15} = 0.32$ | $n_{15} = 1.648$ | $v_{15} = 33.79$ |
| $S_{16}$ | $r_{16} = 1.762$ | $d_{16} = 0.11$ | | |

-continued

LENS DATA (1)
Viewing Angle (2ω) = 60°
Distance to Object = 11.7

| | | | | |
|---|---|---|---|---|
| $S_{17}$ | $r_{17} = \infty$ (Iris Diaphragm) | $d_{17} = 0.03$ | | |
| $S_{18}$ | $r_{18} = \infty$ | $d_{18} = 0.5$ | $n_{18} = 1.516$ | $v_{18} = 64.14$ |
| $S_{19}$ | $r_{19} = \infty$ | $d_{19} = 0.09$ | | |
| $S_{20}$ | $r_{20} = \infty$ | $d_{20} = 1.2$ | $n_{20} = 1.883$ | $v_{20} = 40.78$ |
| $S_{21}$ | $r_{21} = \infty$ | $d_{21} = 0.1$ | | |
| $S_{22}$ | $r_{22} = 3.625$ | $d_{22} = 1.1$ | $n_{22} = 1.847$ | $v_{22} = 23.78$ |
| $S_{23}$ | $r_{23} = 1.322$ | $d_{23} = 1.92$ | $n_{23} = 1.729$ | $v_{23} = 54.68$ |
| $S_{24}$ | $r_{24} = -5.682$ | $d_{24} = 0.83$ | | |
| $S_{25}$ | $r_{25} = \infty$ | $d_{25} = 1.6$ | $n_{25} = 1.514$ | $v_{25} = 75.00$ |
| $S_{26}$ | $r_{26} = \infty$ | $d_{26} = 0.79$ | $n_{26} = 1.516$ | $v_{26} = 64.15$ |
| $S_{27}$ | $r_{27} = \infty$ | $d_{27} = 0.5$ | $n_{27} = 1.497$ | $v_{27} = 81.61$ |
| $S_{28}$ | $r_{28} = \infty$ | | | | where rn denotes a radius of curvature, dn denotes the thickness of a lens (prism) or an aerial distance, nn denotes the refractive index of a glass material, and vn denotes the Abbe number of a glass material.

The optical axis of the relay optical system 13 must be aligned with the direction of the optical axes of the objective optical systems 10a and 10b. The positions of the exit pupils of the objective optical systems 10a and 10b must be set to infinitely far positions. Peripheral light must not be lost. The objective optical systems 10a and 10b may be formed with, for example, telecentric systems.

The cover glasses 29 prevent adhesive traces or other dust from falling on the image planes and being projected as part of optical images. If dust should adhere to the surfaces of the cover glasses 29, the dust or the like adhering to the surfaces would interfere with clear visualization of endoscopic images. This is because the surfaces of the cover glasses 29 are separated from the image planes of the objective optical systems 10a and 10b. Observation will therefore not be hindered in practice.

As mentioned above, the optical adaptor of the present embodiment is composed of or divided into the first frame member in which two objective optical systems sharing the same specifications are stowed and the second frame member in which the relay optical system is stowed. The structure of the frame member itself in which each optical system is stowed is identical to that of a frame member adopted for a conventional product. The frame members can therefore be assembled according to an assembling technology employed in the conventional product. The assembling is easy.

The two frame members are mechanically coupled to each other with a distance restriction member, of which dimensions are strictly precise, therebetween. A difference in observable depth that may occur between products can be minimized.

In the present embodiment, the imaging device stowage portion, in which the CCD that requires a large space and other elements are stowed, is located behind where the adaptor attachment/detachment member reaches to make the diameter of the endoscope small. Even when an endoscope has a system of lenses, of which diameters are small, located ahead of an imaging device away from the adaptor attachment/detachment member, optical images are transmitted to an optical system in the main endoscope unit via a relay optical system. The optical images can therefore be transmitted according to the size of lenses incorporated in the main endoscope unit.

Owing to the components, although the optical adaptor requires a plurality of objective optical systems and has a complex structure, the components can be assembled readily. The distance between the plurality of objective optical systems and relay optical system can be set precisely. There is no difference in observable depth between products. Owing to the optical adaptor for an endoscope, the distal endoscope part, to which the adaptor having the objective optical systems and relay optical system incorporated therein is attached, can be thinned, and the outer diameter of the optical adaptor can be made duly small.

The cover glasses, distal plano-convex lenses, distance rings, rear plano-convex lenses, mask, and cover glass that are stowed in the first frame member are locked and held in the first frame member using an adhesive. Similarly, the plurality of lenses, the plurality of distance rings, and the cover glass stowed in the second frame member are locked and held in the second frame member using an adhesive. The members are therefore reliably prevented from moving due to external influence. Consequently, the specifications of each lens including a power do not fluctuate because of small movement of the lens, which could adversely effect measurement.

In the present embodiment, the optical adaptor is a binocular optical adaptor including the two objective optical systems sharing the same specifications. The present invention is not limited to this type of optical adaptor. Alternatively, an optical adaptor having three objective optical systems having different specifications may be used. In this case, three optical images are projected on the imaging device via a mask having three or more openings. An optical adaptor having a plurality of objective optical systems with specifications that are different from the specifications shared by the objective optical systems may be used.

Referring to FIG. 9 to FIG. 12, the second embodiment of the present invention will be described below.

Figure 9:
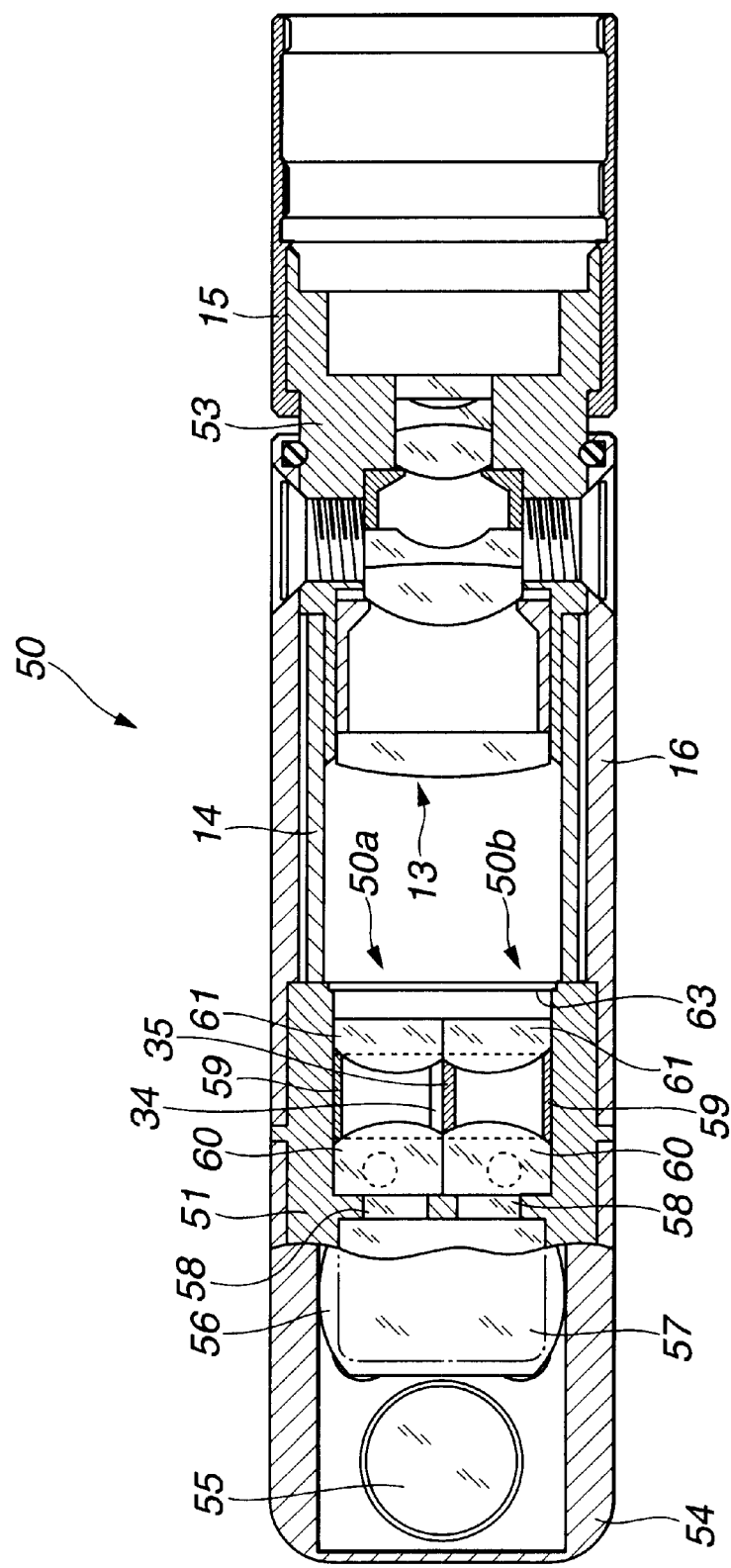
Figure 10:
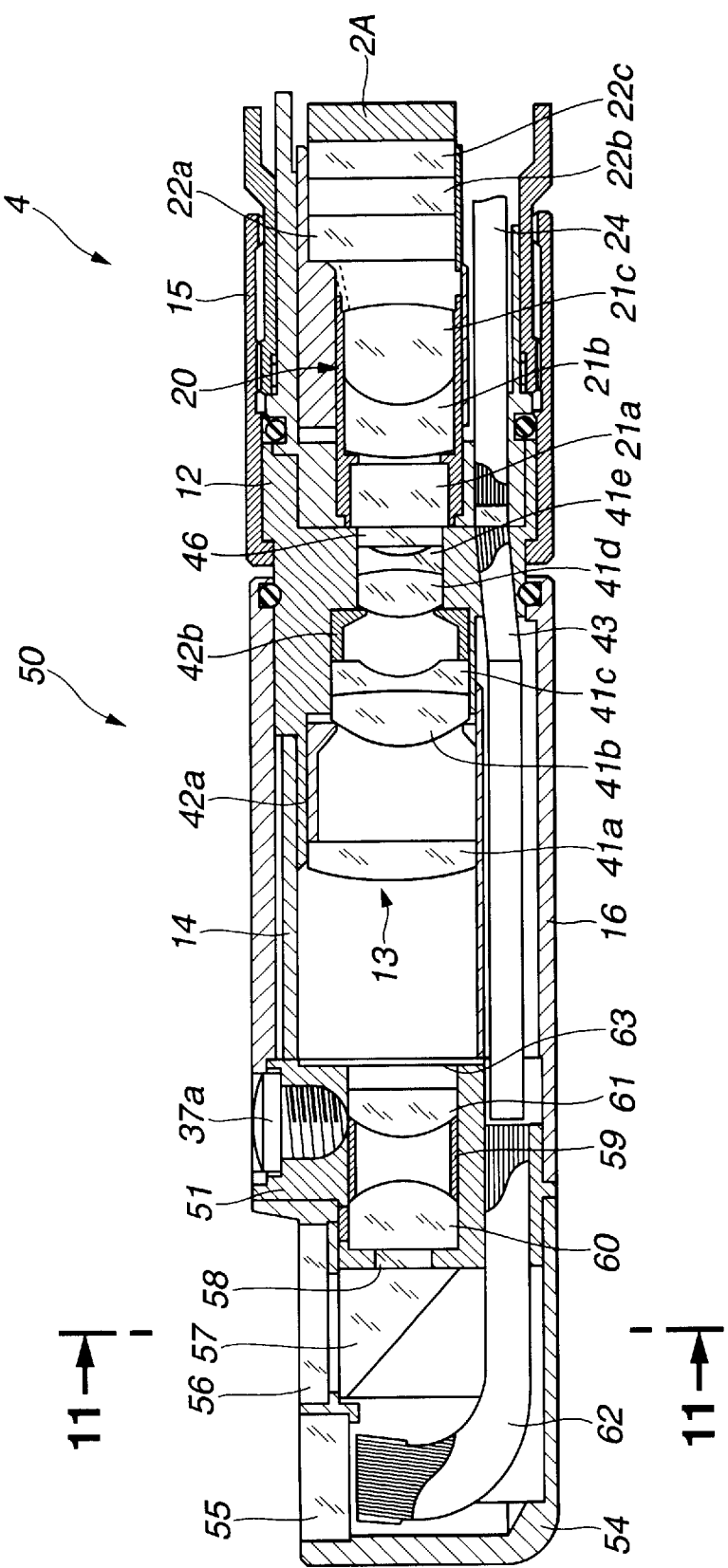

The optical adaptor 9 of the first embodiment is a direct-view optical system. Herein, light is emitted in a direction of insertion. An optical image of a region to be examined, which is located in direct view and illuminated with the light, is acquired by the objective optical systems 10a and 10b. By contrast, an optical adaptor 50 of the present embodiment is such that light is, as shown in FIG. 9 and FIG. 10, emitted through an illumination cover glass 55 orthogonal to a direction of insertion, that is, placed in a direction of a side view. An optical image of a region to be examined, which is illuminated with the light and located in the direction of the side view, is acquired by the two objective optical systems 50a and 50b via a side-view observation cover glass 56. The objective optical systems 50a and 50b are stowed in a first frame member 51 and share the same specifications. Resultant optical images are then projected on an imaging device 2A in the endoscope 1.

In the first frame member 51, an integral part of the optical adaptor 50 of the present embodiment, pairs of plano-convex lenses 60 and 61 in the two objective optical systems 50a and 50b are, like those of the first embodiment, separated by a predetermined distance with two distance rings 59. The plano-convex lenses 60 and 61 are stowed in a plano-convex lens stowage portion (not shown) shaped substantially like a numeral 8. One prism 57 is placed in front of two side-view cover glasses 58 located in front of the plano-convex lenses 60 so that the prism will cover all or at least part of a range of observation defined by the two objective optical systems 50a and 50b. The prism 57 serves as a deflecting element for deflecting an optical axis by 90° and thus changing the direction of a field of view.

A side-view light guide fiber bundle 62 over which light used to illuminate a region located in the direction of side view is propagated is secured using an adhesive with an optical path deflected substantially 90° in line with the prism 57. One end of the side-view light fiber bundle 62 is located in front of the prism. The proximal end thereof is opposed to an emission end of the adaptor light guide fiber bundle 43 in the second frame member 12.

A distal cover member 54 in the first frame member 51 will cover the side-view light guide fiber bundle 62 and prism 57 located in the distal part of the first frame member. The distal cover member 54 is fixed as an integral part to the first frame member 51 using a screw 37*a*.

In the distal cover member 54, the illumination cover glass 55 and side-view observation cover glass 56 are placed. Through the illumination cover glass 55, light propagated over the adaptor light guide fiber bundle 43 and side-view light guide fiber bundle 62 is emitted in the direction of the side view. Through the side-view observation cover glass 56 located proximally to the illumination cover glass 55, an optical image of a region to be examined, which is illuminated with the light, is routed to the objective optical systems 50*a* and 50*b* via the prism 57.

One side of the side-view observation cover glass 56 opposed to the illumination cover glass 55 is cut flat in order to avoid interference with the illumination cover glass 55. The side-view observation cover glass 56 is therefore shaped like the letter D.

The optical adaptor 50 of the present embodiment is made by mechanically fixing the first frame member 51 and second frame member 12 to the adaptor body 16 with the distance restriction member 14 therebetween in the same manner as in the first embodiment. The side view light guide fiber bundle 62, prism 57, and two objective optical systems 50*a* and 50*b* are stowed in the distal part of the first frame member 51. The relay optical system 13 is stowed in the second frame member 12. The distance restriction member 14 sets the distance between the frame members 51 and 12 to a predetermined value. Thereafter, the distal cover member 54 is fixed as an integral part to the distal end of the first frame member 51.

Consequently, an optical image of a region to be examined, which is located in the side view direction, acquired through the side-view cover glass 58 is deflected 90° by the prism 57 and propagated into the objective optical systems 50*a* and 50*b*. Resultant optical images are then passed through the relay optical system 13 and objective optical system 20 in the endoscope and projected on the imaging surface of the imaging device 2A.

Since the optical adaptor 50 is fixed to the distal part 4, an optical path along which an optical image passes through the objective optical system 50*a* or 50*b* is projected on the imaging device 2A is defined as shown in FIG. 12. The data of the lenses will be listed below. Since the objective optical systems 50*a* and 50*b* share the same specifications, only one data set will be presented.

LENS DATA (2)
Viewing Angle (2ω) = 60°
Distance to Object = 13

| | | | | |
|---|---|---|---|---|
| $S_1$ | $r_1 = \infty$ | $d_1 = 0.5$ | $n_1 = 1.883$ | $v_1 = 40.76$ |
| $S_2$ | $r_2 = \infty$ | $d_2 = 0.2$ | | |
| $S_3$ | $r_3 = \infty$ | $d_3 = 2.6$ | $n_3 = 1.883$ | $v_3 = 40.76$ |
| $S_4$ | $r_4 = \infty$ | $d_4 = 0.3$ | | |
| $S_5$ | $r_5 = \infty$ | $d_5 = 1.12$ | $n_5 = 1.835$ | $v_5 = 42.72$ |
| $S_6$ | $r_6 = -2.297$ | $d_6 = 0.54$ | | |
| $S_7$ | $r_7 = 2.297$ | $d_7 = 1.12$ | $n_7 = 1.835$ | $v_7 = 42.72$ |

-continued

LENS DATA (2)
Viewing Angle (2ω) = 60°
Distance to Object = 13

| | | | | |
|---|---|---|---|---|
| $S_8$ | $r_8 = \infty$ | $d_8 = 0.74$ | | |
| $S_9$ | $r_9 = \infty$ (Field Stop) | $d_9 = 0.03$ | | |
| $S_{10}$ | $r_{10} = \infty$ | $d_{10} = 3.61$ | | |
| $S_{11}$ | $r_{11} = 7.721$ | $d_{11} = 0.8$ | $n_{11} = 1.883$ | $v_{11} = 40.76$ |
| $S_{12}$ | $r_{12} = \infty$ | $d_{12} = 1.84$ | | |
| $S_{13}$ | $r_{13} = 2.024$ | $d_{13} = 1.03$ | $n_{13} = 1.773$ | $v_{13} = 49.60$ |
| $S_{14}$ | $r_{14} = -12.96$ | $d_{14} = 0.3$ | $n_{14} = 1.593$ | $v_{14} = 35.31$ |
| $S_{15}$ | $r_{15} = 1.009$ | $d_{15} = 1.2$ | | |
| $S_{16}$ | $r_{16} = 1.686$ | $d_{16} = 0.88$ | $n_{16} = 1.773$ | $v_{16} = 49.60$ |
| $S_{17}$ | $r_{17} = 4.362$ | $d_{17} = 0.32$ | $n_{17} = 1.648$ | $v_{17} = 33.79$ |
| $S_{18}$ | $r_{18} = 1.762$ | $d_{18} = 0.11$ | | |
| $S_{19}$ | $r_{19} = \infty$ (Iris Diaphragm) | $d_{19} = 0.03$ | | |
| $S_{20}$ | $r_{20} = \infty$ | $d_{20} = 0.5$ | $n_{20} = 1.516$ | $v_{20} = 64.14$ |
| $S_{21}$ | $r_{21} = \infty$ | $d_{21} = 0.09$ | | |
| $S_{22}$ | $r_{22} = \infty$ | $d_{22} = 1.2$ | $n_{22} = 1.883$ | $v_{22} = 40.78$ |
| $S_{23}$ | $r_{23} = \infty$ | $d_{23} = 0.1$ | | |
| $S_{24}$ | $r_{24} = 3.625$ | $d_{24} = 1.1$ | $n_{24} = 2.847$ | $v_{24} = 23.78$ |
| $S_{25}$ | $r_{25} = 1.322$ | $d_{25} = 1.92$ | $n_{25} = 1.729$ | $v_{25} = 54.68$ |
| $S_{26}$ | $r_{26} = -5.682$ | $d_{26} = 0.83$ | | |
| $S_{27}$ | $r_{27} = \infty$ | $d_{27} = 1.6$ | $n_{27} = 1.514$ | $v_{27} = 75.00$ |
| $S_{28}$ | $r_{28} = \infty$ | $d_{28} = 0.79$ | $n_{28} = 1.516$ | $v_{28} = 64.15$ |
| $S_{29}$ | $r_{29} = \infty$ | $d_{29} = 0.5$ | $n_{29} = 1.497$ | $v_{29} = 81.61$ |
| $S_{30}$ | $r_{30} = \infty$ | | | | where rn denotes a radius of curvature, dn denotes the thickness of a lens (prism) or an aerial distance, nn denotes the refractive index of a glass material, and vn denotes the Abbe number of a glass material.

A mask 63 having two octagonal openings is, similarly to that of the first embodiment, placed on the image planes of the objective optical systems 50*a* and 50*b* and fixed to the first frame member 51. The contours of the two octagonal openings are clearly delineated on the imaging device 2A.

In the present embodiment, the proximal end surfaces of the rear plano-convex lenses 61 of the objective optical systems 50*a* and 50*b* are located in a dented place located distally to the mask 63. Owing to this structure, when dust or the like adheres to the surfaces of the plano-convex lenses 61, since the surfaces are separated from the imaging surface of the imaging device 2A, the dust adhering the surfaces will not be clearly seen as part of an endoscopic image.

The optical adaptor 50 is designed so that the end of the side-view light guide fiber bundle 62 is fixed to the first frame member 51 using an adhesive in order to illuminate a region to be examined that is located in the side view direction. The present invention is not limited to this structure. Alternatively, a means for bending the adaptor light guide fiber bundle 43 within the first frame member 51 may be used to illuminate a region to be examined that is located in the side view direction.

The other components are identical to those of the first embodiment. The same reference numerals will be assigned to the identical components, and the description of the components will be omitted.

As mentioned above, the side-view light guide fiber bundle and prism are included in the distal part of the first frame member in which the two objective optical systems sharing the same specifications are stowed. The side-view light guide fiber bundle supplies light in the side view direction. The prism introduces an optical image acquired in the side view direction into the two objective optical systems sharing the same specifications. The distal part of the first frame member is covered with the distal cover member having the illumination cover glass and side-view observation cover glass opposed to the side-view light guide fiber bundle and prism. Thus, the optical adaptor used to observe a region located in the side view direction is constructed readily The other operations and advantages are identical to those of the first embodiment.

Referring to FIG. 13A to FIG. 15B, the third embodiment of the present invention will be described below.

In the second embodiment, the two objective optical systems in the side view type optical adaptor 50 share the same specifications. By contrast, in the present embodiment, two objective optical systems in an optical adaptor 50A have different specifications. The components of the present embodiment will be described more particularly below.

As shown in FIG. 13A and FIG. 13B, the optical adaptor 50A of the present embodiment has two objective optical systems 80 and 90 with different specifications. The center positions of side-view cover glasses 81 and 91 associated with the objective optical systems 80 and 90, which are located on the optical axes of the objective optical systems, are offset in a direction of insertion. In other words, optical paths defined with the objective optical systems 80 and 90 are different.

The two objective optical systems 80 and 90 defining optical paths of different lengths, and prisms 82 and 92 located at the distal ends of the objective optical systems 80 and 90 are stowed in a first frame member 71 of the optical adaptor 50A of the present embodiment. The prisms 82 and 92 deflect an optical image of a region to be examined, which is located in the side view direction, by 90° so that the optical image will be propagated into the objective optical systems 80 and 90. The positions on the prisms 82 and 92 at which the optical image is deflected are different along the direction of insertion.

The structures of the objective optical systems 80 and 90 will be described below.

As shown in FIGS. 13B and 14A, the objective optical system 80 is located behind the emission surface of the prism 82. The objective optical system 80 is composed of a first planar parallel plate 83, plano-convex lenses 84 and 85, a first distance ring 86, a second planar parallel plate 87, and a second distance ring 88 that are arranged in that order from the distal end of the objective optical system. The first planar parallel plate 83 transmits an optical image. The first distance ring 86 maintains the distance between the plano-convex lenses 84 and 85 at a predetermined value. The second planar parallel plate 87 for transmitting an optical image abuts on the proximal surface of the plano-convex lens 85. The second distance ring 88 has a predetermined length.

As shown in FIGS. 13B and 14B, the objective optical system 90 is located behind the emission surface of the prism 92. The objective optical system 90 is composed of a first distance ring 931 plano-convex lenses 94 and 95, a second distance ring 96, and a third distance ring 97 that are arranged in that order from the distal end of the optical system. The first distance ring 93 has a predetermined length. The second distance ring 96 maintains the distance between the plano-convex lenses 94 and 95 at a predetermined value. The third distance ring 97 abuts on the proximal surface of the plano-convex lens 85 and has a predetermined length.

The objective optical system 80 and the objective optical system 90 have the plano-convex lenses 84, 85, 94, and 95 as well as the plurality of plane parallel plates 83 and 87 or the plurality of distance rings 86, 88, 93, 96, and 97 arranged properly. The prisms 82 and 92 are positioned to deflect light. Optical images emitted from the prisms 82 and 92 pass through the objective optical systems 80 and 90 and project onto the same surface.

The plano-convex lenses 84, 85, 94, and 95, the distance rings 86, 88, 93, 96, and 97, and the planar parallel plates 83 and 87 constituting the objective optical systems 80 and 90 are stowed in a plano-convex lens stowage portion (not shown). The plano-convex lens stowage portion is, like those of the aforesaid embodiments, a through hole of the first frame member 71 shaped substantially like the numeral 8.

The distal part of the first frame member 71 is, similarly to the one of the second embodiment, covered with a distal cover member 72. In the distal cover member 72, the side-view cover glasses 81 and 91 oppose the incidence surfaces of the prisms 82 and 92.

An illumination cover glass 73 for emitting light, which has been propagated over the sideview light guide fiber bundle 62, in the side view direction is located in front of the side-view cover glass 91.

Owing to the foregoing structure, an optical image of a region to be examined, which is located in the side view direction and illuminated with light emitted from the illumination cover glass 73, passes through the side-view cover glasses 81 and 91 and the prisms 82 and 92 stowed in the first frame member 71. The resultant optical images are then propagated into the objective optical systems 80 and 90 having different specifications.

The optical adaptor 50A of the present embodiment is made by mechanically fixing the first frame member 71 and second frame member 12 to the adaptor body 16 with the distance restriction member 14 therebetween in the same manner as that of the first embodiment. The side view light guide fiber bundle 62, prisms 82 and 92, and objective optical systems 80 and 90 are stowed in the distal part of the first frame member 71. The relay optical system 13 is stowed in the second frame member 12. The distance restriction member 14 sets the distance between the frame members 71 and 12 to a predetermined value, Thereafter, the distal cover member 72 is fixed as an integral part to the distal part of the first frame member 71.

Consequently, an optical image of a region to be examined that is located in the side view direction is acquired through the side-view cover glasses 81 and 91. Resultant optical images are deflected 90° by the prisms 82 and 92 opposed to the side-view cover glasses 81 and 91, and propagated into the objective optical systems 80 and 90. The optical images are then projected on the imaging device 2A through the relay optical system 13 and the objective optical system 20 in the endoscope.

Since the optical adaptor 50 is fixed to the distal part 4, optical paths along which optical images propagated into the objective optical systems 80 and 90 are projected on the imaging device 2A are defined as shown in FIG. 15A and FIG. 15B. The data of the lenses will be listed below. First, the data of the lenses including those constituting the objective optical system 80 will be listed.

LENS DATA (3)
Viewing Angle ($2\omega$) = 20°
Distance to Object = 29.9

| | | | | |
|---|---|---|---|---|
| $S_1$ | $r_1 = \infty$ | $d_1 = 0.5$ | $n_1 = 1.883$ | $v_1 = 40.76$ |
| $S_2$ | $r_2 = \infty$ | $d_2 = 0.2$ | | |
| $S_3$ | $r_3 = \infty$ | $d_3 = 2.6$ | $n_3 = 1.883$ | $v_3 = 40.76$ |
| $S_4$ | $r_4 = \infty$ | $d_4 = 0.1$ | | |
| $S_5$ | $r_5 = \infty$ | $d_5 = 4.56$ | $n_5 = 1.883$ | $v_5 = 40.76$ |
| $S_6$ | $r_6 = \infty$ | $d_6 = 1.25$ | $n_6 = 1.729$ | $v_6 = 54.68$ |
| $S_7$ | $r_7 = -5.202$ | $d_7 = 2.8$ | | |

-continued

LENS DATA (3)
Viewing Angle (2ω) = 20°
Distance to Object = 29.9

| | | | | |
|---|---|---|---|---|
| $S_8$ | $r_8 = 5.202$ | $d_8 = 1.25$ | $n_8 = 1.729$ | $v_8 = 54.68$ |
| $S_9$ | $r_9 = \infty$ | $d_9 = 2.9$ | $n_9 = 1.883$ | $v_9 = 40.76$ |
| $S_{10}$ | $r_{10} = \infty$ | $d_{10} = 1.0$ | | |
| $S_{11}$ | $r_{11} = \infty$ (Field Stop) | $d_{11} = 0.03$ | | |
| $S_{12}$ | $r_{12} = \infty$ | $d_{12} = 3.61$ | | |
| $S_{13}$ | $r_{13} = 7.721$ | $d_{13} = 0.8$ | $n_{13} = 1.883$ | $v_{13} = 40.76$ |
| $S_{14}$ | $r_{14} = \infty$ | $d_{14} = 1.84$ | | |
| $S_{15}$ | $r_{15} = 2.024$ | $d_{15} = 1.03$ | $n_{15} = 1.773$ | $v_{15} = 49.60$ |
| $S_{16}$ | $r_{16} = 12.96$ | $d_{16} = 0.3$ | $n_{16} = 1.593$ | $v_{16} = 35.31$ |
| $S_{17}$ | $r_{17} = 1.009$ | $d_{17} = 1.2$ | | |
| $S_{18}$ | $r_{18} = 1.686$ | $d_{18} = 0.88$ | $n_{18} = 1.773$ | $v_{18} = 49.60$ |
| $S_{19}$ | $r_{19} = -4.362$ | $d_{19} = 0.32$ | $n_{19} = 1.648$ | $v_{19} = 33.79$ |
| $S_{20}$ | $r_{20} = 1.762$ | $d_{20} = 0.11$ | | |
| $S_{21}$ | $r_{21} = \infty$ (Iris Diaphragm) | $d_{21} = 0.03$ | | |
| $S_{22}$ | $r_{22} = \infty$ | $d_{22} = 0.4$ | $n_{22} = 1.516$ | $v_{22} = 64.14$ |
| $S_{23}$ | $r_{23} = \infty$ | $d_{23} = 0.09$ | | |
| $S_{24}$ | $r_{24} = \infty$ | $d_{24} = 1.2$ | $n_{24} = 1.883$ | $v_{24} = 40.78$ |
| $S_{25}$ | $r_{25} = \infty$ | $d_{25} = 0.1$ | | |
| $S_{26}$ | $r_{26} = 3.567$ | $d_{26} = 1.0$ | $n_{26} = 1.847$ | $v_{26} = 23.78$ |
| $S_{27}$ | $r_{27} = 1.273$ | $d_{27} = 2.02$ | $n_{27} = 1.729$ | $v_{27} = 54.68$ |
| $S_{28}$ | $r_{28} = 5.682$ | $d_{28} = 0.83$ | | |
| $S_{29}$ | $r_{29} = \infty$ | $d_{29} = 1.6$ | $n_{29} = 1.514$ | $v_{29} = 75.00$ |
| $S_{30}$ | $r_{30} = \infty$ | $d_{30} = 0.79$ | $n_{30} = 1.516$ | $v_{30} = 64.15$ |
| $S_{31}$ | $r_{31} = \infty$ | $d_{31} = 0.5$ | $n_{31} = 1.497$ | $v_{31} = 81.61$ |
| $S_{32}$ | $r_{32} = \infty$ | | | | where rn denotes a radius of curvature, dn denotes the thickness of a lens (prism) or an aerial distance, nn denotes the refractive index of a glass material, and vn denotes the Abbe number of a glass material. Next, the data of the lenses including those constituting the objective optical system 90 will be listed.

LENS DATA (4)
Viewing Angle (2ω) = 20°
Distance to Object = 29.9

| | | | | |
|---|---|---|---|---|
| $S_1$ | $r_1 = \infty$ | $d_1 = 0.5$ | $n_1 = 1.883$ | $v_1 = 40.76$ |
| $S_2$ | $r_2 = \infty$ | $d_2 = 0.2$ | | |
| $S_3$ | $r_3 = \infty$ | $d_3 = 2.6$ | $n_3 = 1.883$ | $v_3 = 40.76$ |
| $S_4$ | $r_4 = \infty$ | $d_4 = 2.52$ | | |
| $S_5$ | $r_5 = \infty$ | $d_5 = 1.25$ | $n_5 = 1.729$ | $v_5 = 54.68$ |
| $S_6$ | $r_6 = -5.202$ | $d_6 = 2.8$ | | |
| $S_7$ | $r_7 = 5.202$ | $d_7 = 1.25$ | $n_7 = 1.729$ | $v_7 = 54.68$ |
| $S_8$ | $r_8 = \infty$ | $d_8 = 2.54$ | | |
| $S_9$ | $r_9 = \infty$ (Field stop) | $d_9 = 0.03$ | | |
| $S_{10}$ | $r_{10} = \infty$ | $d_{10} = 3.61$ | | |
| $S_{11}$ | $r_{11} = 7.721$ | $d_{11} = 0.8$ | $n_{11} = 1.883$ | $v_{11} = 40.76$ |
| $S_{12}$ | $r_{12} = \infty$ | $d_{12} = 1.84$ | | |
| $S_{13}$ | $r_{13} = 2.024$ | $d_{13} = 1.03$ | $n_{13} = 1.773$ | $v_{13} = 49.60$ |
| $S_{14}$ | $r_{14} = -12.96$ | $d_{14} = 0.3$ | $n_{14} = 1.593$ | $v_{14} = 35.31$ |
| $S_{15}$ | $r_{15} = 1.009$ | $d_{15} = 1.2$ | | |
| $S_{16}$ | $r_{16} = 1.686$ | $d_{16} = 0.88$ | $n_{16} = 1.773$ | $v_{16} = 49.60$ |
| $S_{17}$ | $r_{17} = -4.362$ | $d_{17} = 0.32$ | $n_{17} = 1.648$ | $v_{17} = 33.79$ |
| $S_{18}$ | $r_{18} = 1.762$ | $d_{18} = 0.11$ | | |
| $S_{19}$ | $r_{19} = \infty$ (Iris Diaphragm) | $d_{19} = 0.03$ | | |
| $S_{20}$ | $r_{20} = \infty$ | $d_{20} = 0.4$ | $n_{20} = 1.516$ | $v_{20} = 64.14$ |
| $S_{21}$ | $r_{21} = \infty$ | $d_{21} = 0.09$ | | |
| $S_{22}$ | $r_{22} = \infty$ | $d_{22} = 1.2$ | $n_{22} = 1.883$ | $v_{22} = 40.78$ |
| $S_{23}$ | $r_{23} = \infty$ | $d_{23} = 0.1$ | | |
| $S_{24}$ | $r_{24} = 3.567$ | $d_{24} = 1.0$ | $n_{24} = 1.847$ | $v_{24} = 23.78$ |
| $S_{25}$ | $r_{25} = 1.273$ | $d_{25} = 2.02$ | $n_{25} = 1.729$ | $v_{25} = 54.68$ |
| $S_{26}$ | $r_{26} = -5.682$ | $d_{26} = 0.83$ | | |
| $S_{27}$ | $r_{27} = \infty$ | $d_{27} = 1.6$ | $n_{27} = 1.514$ | $v_{27} = 75.00$ |
| $S_{28}$ | $r_{28} = \infty$ | $d_{28} = 0.79$ | $n_{28} = 1.516$ | $v_{28} = 64.15$ |
| $S_{29}$ | $r_{29} = \infty$ | $d_{29} = 0.5$ | $n_{29} = 1.497$ | $v_{29} = 81.61$ |
| $S_{30}$ | $r_{30} = \infty$ | | | | where rn denotes a radius of curvature, dn denotes the thickness of a lens (prism) or an aerial distance, nn denotes the refractive index of a glass material, and vn denotes the Abbe number of a glass material.

The other components are identical to those of the second embodiment. The same reference numerals will be assigned to the identical components, and the description of the components will be omitted.

As mentioned above, the optical adaptor is constructed using the two objective optical systems that define optical paths of different lengths and have different specifications. The center positions of the side-view cover glasses opposed to the prisms in the objective optical systems, which are located on the optical axes of the objective optical systems, are offset along the direction of insertion. Consequently, a large parallax can be attained from the distance between the optical axes of the objective optical systems.

Images formed by the two objective optical systems having different specifications are projected onto one CCD. For measuring an object according to a known trigonometric survey method, the distance between the objective optical systems need not be increased. A parallax larger than the distance can be attained, thus measurement can be achieved highly precisely. The other operations and advantages are identical to those of the first embodiment.

In the present invention, it is apparent that a wide range of different embodiments can be constructed based on the present invention without a departure from the spirit and scope of the invention. This invention will be limited by the appended claims but not be restricted by any specific embodiments.

What is claimed is:

1. An optical adaptor for an endoscope comprising:
a first frame member located at a distal part of said optical adaptor and having a plurality of objective optical systems stowed and held therein;
a second frame member located behind said plurality of objective optical systems and having a relay optical system, which transmits optical images formed by said objective optical systems and cooperates with an imaging optical system located in front of an imaging device in an endoscope to form an image transmission optical system, stowed and held therein; and
a distance restriction member, interposed between said first frame member and second frame member, for setting a distance between said first frame member and said second frame member to a predetermined value.

2. An optical adaptor for an endoscope according to claim 1, wherein said first frame member has a through hole, shaped substantially like a numeral 8, therein so that members constituting said objective optical systems can be arranged in the through hole.

3. An optical adaptor for an endoscope according to claim 1, wherein said objective optical systems are formed with telecentric systems with exit pupils located at infinite positions.

4. An optical adaptor for an endoscope according to claim 3, wherein members constituting said objective optical systems or relay optical system are fixed to said frame member using an adhesive.

5. An optical adaptor for an endoscope according to claim 1, wherein members constituting said objective optical systems or relay optical system are fixed to said frame member using an adhesive.

6. An optical adaptor for an endoscope according to claim 1, wherein, when said objective optical systems each include a field stop, the field stop and a last surface of each of said objective optical systems are separated.

7. An optical adaptor for an endoscope according to claim 1, further comprising a housing member for shielding said first frame member and second frame member as a unit, wherein, when said first frame member and second frame member are mechanically fixed to said housing member, said distance restriction member for setting the distance between said first frame member and second frame member is located at a predetermined position.

8. An optical adaptor for an endoscope according to claim 7, wherein said first frame member has a through hole, shaped substantially like a numeral 8, therein so that members constituting said objective optical systems can be arranged in the through hole.

9. An optical adaptor for an endoscope according to claim 7, wherein said objective optical systems are formed with telecentric systems with exit pupils located at infinite positions.

10. An optical adaptor for an endoscope according to claim 7, wherein a deflection element for deflecting a direction of a field of view is located in front of said plurality of objective optical systems stowed and held in said first frame member.

11. An optical adaptor for an endoscope according to claim 10, wherein only one deflection element is arranged relative to said plurality of objective optical systems.

12. An optical adaptor for an endoscope according to claim 10, wherein members constituting said objective optical systems or relay optical system are fixed to said frame member using an adhesive.

13. An optical adaptor for an endoscope according to claim 7, wherein deflection elements for deflecting light in a same direction are arranged in one-to-one correspondence with said plurality of objective optical systems stowed and held in said first frame member, wherein positions on said deflection elements at which light is deflected are different along a direction of insertion, and wherein positions of image planes of said plurality of objective optical systems are at the same position along the direction of insertion.

14. An optical adaptor for an endoscope according to claim 13, wherein members constituting said objective optical systems or relay optical system are fixed to said frame member using an adhesive.

15. An optical adaptor for an endoscope according to claim 7, wherein members constituting said objective optical systems or relay optical system are fixed to said frame member using an adhesive.

16. An optical adaptor for an endoscope according to claim 7, wherein, when said objective optical systems each include a field stop, the field stop and a last surface of each of said objective optical systems are separated.

* * * * *